(12) United States Patent
Ni et al.

(10) Patent No.: US 10,048,183 B2
(45) Date of Patent: Aug. 14, 2018

(54) INTEGRATED STYLE SHEAR APPARATUS FOR ROCK STRUCTURAL PLANE AND A SHEAR EXPERIMENTAL METHOD FOR ROCK STRUCTURAL PLANE

(71) Applicant: POWERCHINA HUADONG ENGINEERING CORPORATION LIMITED, Hangzhou, Zhejiang (CN)

(72) Inventors: Weida Ni, Zhejiang (CN); Zhigang Shan, Zhejiang (CN); Anchi Shi, Zhejiang (CN); Jingyong Wang, Zhejiang (CN); Wanqiang Cheng, Zhejiang (CN); Miaojun Sun, Zhejiang (CN)

(73) Assignee: Powerchina Huadong Engineering Corporation Limited, Zhejiang (CN)

( * ) Notice: Subject to any disclaimer, the term of this patent is extended or adjusted under 35 U.S.C. 154(b) by 57 days.

(21) Appl. No.: 15/334,756

(22) Filed: Oct. 26, 2016

(65) Prior Publication Data
US 2017/0284911 A1    Oct. 5, 2017

(30) Foreign Application Priority Data
Mar. 31, 2016   (CN) .......................... 2016 1 0203652

(51) Int. Cl.
*G01N 3/24* (2006.01)
(52) U.S. Cl.
CPC ....... *G01N 3/24* (2013.01); *G01N 2203/0003* (2013.01); *G01N 2203/0025* (2013.01); *G01N 2203/0048* (2013.01)

(58) Field of Classification Search
CPC ... G01N 3/24; G01N 3/00; G01R 1/04; G01R 1/06722; G01R 1/073; G01R 31/01; G01R 31/28
See application file for complete search history.

(56) References Cited

U.S. PATENT DOCUMENTS

| 3,854,328 | A | * | 12/1974 | Schmidt | ................... | G01N 3/32 |
|||||||  73/803 |
| 3,975,950 | A | * | 8/1976 | Erdei | ....................... | G01N 3/10 |
|||||||  73/790 |
| 4,149,407 | A | * | 4/1979 | Strom | ....................... | G01N 3/36 |
|||||||  73/794 |

(Continued)

FOREIGN PATENT DOCUMENTS

CN          101034088 A  *  9/2007

OTHER PUBLICATIONS

English translation of CN 101034088 A.*

*Primary Examiner* — Harshad R. Patel
*Assistant Examiner* — Tran M Tran
(74) *Attorney, Agent, or Firm* — Muncy, Geissler, Olds & Lowe, P.C.

(57) ABSTRACT

An integrated-style shear apparatus for testing a rock structural plane includes a frame system, a vertical loading system, a horizontal loading system, and a shearing system. Both the vertical loading system and the horizontal loading system are fixed on the frame system, and the shearing system is installed inside the frame system. The shearing system is used to prepare the sample of structural plane and actualize the shear test. The vertical loading system and the horizontal loading system are used to provide normal stress and shear stress for the shearing system respectively.

7 Claims, 4 Drawing Sheets

(56) References Cited

U.S. PATENT DOCUMENTS

| | | | | |
|---|---|---|---|---|
| 4,539,851 | A * | 9/1985 | Lutenegger | G01N 3/24 73/784 |
| 4,579,003 | A * | 4/1986 | Riley | G01N 3/10 73/784 |
| 4,715,212 | A * | 12/1987 | Johanson | G01N 3/08 73/38 |
| 4,854,175 | A * | 8/1989 | Budhu | G01N 3/24 73/841 |
| 4,885,941 | A * | 12/1989 | Vardoulakis | G01N 3/08 73/794 |
| 5,025,668 | A * | 6/1991 | Sarda | G01N 3/10 73/795 |
| 5,063,785 | A * | 11/1991 | Labuz | G01N 3/10 73/821 |
| 5,243,855 | A * | 9/1993 | Stieger | E21B 49/006 73/152.52 |
| 5,253,518 | A * | 10/1993 | Steiger | E21B 49/006 166/250.01 |
| 5,712,431 | A * | 1/1998 | Vilendrer | G01N 3/24 73/841 |
| 5,739,436 | A * | 4/1998 | Trautwein | G01N 3/24 73/841 |
| 5,883,311 | A * | 3/1999 | Hettiarachchi | G01N 3/066 73/799 |
| 6,026,692 | A * | 2/2000 | Brovold | B29C 43/04 73/818 |
| 6,161,422 | A * | 12/2000 | Thomas | G01N 3/08 324/640 |
| 6,598,486 | B2 * | 7/2003 | Vilendrer | G01N 3/24 73/841 |
| 7,191,664 | B2 * | 3/2007 | Thom | G01N 3/08 73/805 |
| 8,656,788 | B2 * | 2/2014 | Jeong | G01N 3/24 73/815 |
| 8,770,038 | B2 * | 7/2014 | Secq | E21B 21/08 73/783 |
| 9,151,154 | B2 * | 10/2015 | Meadows | E21B 49/08 |
| 9,410,874 | B2 * | 8/2016 | He | G01N 3/313 |
| 9,857,278 | B2 * | 1/2018 | Lebedev | G01N 3/00 |
| 9,909,966 | B2 * | 3/2018 | Jiang | G01N 3/24 |
| 2016/0377518 | A1 * | 12/2016 | Puchnin | G01B 7/26 73/12.09 |

* cited by examiner

INTEGRATED STYLE SHEAR APPARATUS FOR ROCK STRUCTURAL PLANE AND A SHEAR EXPERIMENTAL METHOD FOR ROCK STRUCTURAL PLANE

FIELD OF THE INVENTION

The present invention relates to rock mechanics test technology.

BACKGROUND OF THE INVENTION

Indoor direct shear test is the most widely used method for obtaining shear strength and deformation parameters of rock structural plane. However, useful as it is, deficiencies are still exist in traditional indoor direct shear test, for examples: I. During sample preparation, excessive settlement and uneven settlement of the structural plane sample are always inescapable due to the plasticity of cement mortar before initial setting. Therefore, the specifications of structural plane sample are hard to meet the demands of the testing regulation. II. When conducting the test, it is hard for the traditional method to maintain the sheared direction during the process of shearing, due to the undulation of the structural plane. Therefore, the accuracy of the test would be influenced as the sheared direction changed. III. When conducting the test, traditional methods utilized jack and wire rope to exert normal load and shear load, eccentric moment would be caused due to the normal jack is fixed on the upper shear box and the center line of normal load is changed with the sheared displacement of the upper shear box during the process of shearing. Therefore, the outcome of the test would be influenced by the eccentric moment. Besides, the operability and safety of the traditional methods are also need to be improved.

SUMMARY OF THE INVENTION

The major technical problem that the invention needs to be solved is to provide an integrated style direct shear apparatus for rock structural plane which can avoid deficiencies that appeared in sample preparation and experiment of traditional methods, so as to increase the maneuverability of the experiment and the accuracy of its result.

For the purpose of solving the above technical problems, the invention applied technical schemes by using integrated style shear apparatus for rock structural plane, frame system, vertical loading system, horizontal loading system and the shearing system. Both of vertical loading system and horizontal loading system are fixed on, shearing system is installed inside the frame system. The shearing system is used to prepare the sample of structural plane and actualize the shear test, the vertical loading system and the horizontal loading system are used to provide normal stress and shear stress for the shearing system respectively.

The frame system comprises apparatus pedestal, apparatus frame columns, apparatus top panel and limited plate. The bottom of the apparatus frame columns are fixed on the apparatus pedestal and the top of the apparatus frame columns are detachably connected the apparatus top panel through frame column bolts; the apparatus pedestal, the apparatus frame columns and the apparatus top panel formed the frame construction of the entire apparatus, providing operating space for vertical loading system, horizontal loading system and shearing system; limit plate is fixed on the apparatus frame columns; flat jack of vertical loading system is fixed on the apparatus top panel. The apparatus pedestal is equipped with the guide rail groove along with the sheared direction.

The apparatus pedestal is also equipped with sliding assisted device. And the sliding assisted device is combined with rolling ball hole and supported rolling steel ball that located both in a row and uniformly in the surface of the apparatus pedestal; the bottom of the shear box pedestal in the shearing system can connected with rolling steel ball, so as to make it possible for the shear box pedestal to conduct shear displacement with the promotion of horizontal loading system.

The vertical loading system comprises flat jack and rigid plate; and the flat jack is fixed on the apparatus top panel through fixed bolt of flat jack; the nozzle of flat jack penetrated through the apparatus top panel of the frame system and locate at the surface of it; the rigid plate is actively located at the underneath of the flat jack, so as to uniform and stable normal load that provided by the flat jack.

The horizontal loading system comprises horizontal jack and slot for horizontal displacement transducer; and the horizontal jack is fixed on the horizontal jack pedestal through fixed bolt of horizontal jack; the horizontal jack pedestal loaded on the one side of the apparatus pedestal and is connected with the frame system; the horizontal jack is capable of pushing the shear box pedestal in the shear system, so as to conduct shear displacement; the slot for horizontal displacement transducer is set in the horizontal jack pedestal; horizontal displacement transducer that is used to measure the horizontal displacement of shear system is fixed on the inside of the slot for horizontal displacement transducer; the nozzle of horizontal jack is located at the outside of horizontal jack.

The shearing system comprises upper shear box, lower shear box and shear box pedestal; and the location of the upper shear box is limited by the limit plate; the lower shear box can be placed into the shear box pedestal; and the shear box pedestal is equipped with guide rail which enable the shear box pedestal change its place along with the apparatus pedestal; the top of the upper shear box and the bottom of the lower shear box are both equipped with grouting hole.

All round of the upper shear box and the lower shear box are equipped with fastening bolt holes; and each fastening bolt hole is equipped with one sample fastening bolt; the inside end of the sample fastening bolt is detachably loaded fastening rubber gasket.

The upper shear box is equipped with vertical displacement transducer which is used to record the vertical displacement of the upper shear box.

Besides, the present invention also provide a shear experimental method for rock structural plane by using the shear apparatus that is mentioned in above contents, and includes the following steps:

(I). Sample placement: place sample of structural plane into shear box and ensure that the shear direction is consistent with the long edge of the shear box.

(II). Sample adjustment: adjust the position of sample of structural plane and make the shear plane of it higher than the frame of shear box and leveling the shear plane; then, apply the sample fastening bolt and fastening rubber gasket inside the shear box to fix the sample of structural plane.

(III). Sample preparation: inject high strength gypsum paste through the grouting hole located at the bottom of shear box; then, tamp and smooth the gypsum paste. Turn over the sample along with the shear box after gypsum paste's final setting, repeat the above steps to finish the remaining half of the sample; after finishing the sample preparation, backout all the sample fastening bolts.

(IV). Sample loading: pushing prepared sample along with shear boxes into the shear box pedestal of the apparatus and ensure that active shear box is in the lower position while the passive one in the upper position.

(V). Instrument hookup: Horizontal displacement transducer is installed on slot for horizontal displacement transducer of the apparatus; Vertical displacement transducer is installed on the fastening bolt hole of the upper shear box; the No. 1 manually hydraulic pump is connected with nozzle of flat jack and installed digitally hydraulic pressure gauge; the No. 2 manually hydraulic pump is connected with nozzle of horizontal jack and also installed digitally hydraulic pressure gauge. Finally, connected the above transducers and hydraulic gauge with computer and reset all monitoring data.

(VI). Exerting normal stress: using the No. 1 manually hydraulic pump to exert normal stress through vertical loading system and maintain a constant pressure after acquiring specified value.

(VII). Exerting Shearing stress: using the No. 2 manually hydraulic pump to exert, step by step, shearing stress and increasing one level at a certain time, until the sample is cut down.

(VII). Measurement and description of shearing area: after the experiment, measuring the weight of upper part of the sample along with the upper shear box; using cellophane to cover the shearing plane, so as to outline the contour lines around the shearing areas and calculate the shearing area by using the coordinate paper.

(IX). Repeating the experiment: adjusting normal stress of different levels and repeat steps (II) to (V); then, test the rest of samples. It is suggested that the number of samples in each group is around 4 to 5.

(X). Calculating normal stress $\sigma$ and shear stress $\tau$ according to the formula I:

$$\left. \begin{array}{l} \sigma = \dfrac{I_\sigma A_v + G}{A_j} \\ \tau = \dfrac{I_\tau A_h}{A_j} \end{array} \right\} \quad \text{Formula I}$$

where, $\sigma$ is normal stress (MPa); $\tau$ is shear stress (MPa); G is total weight of upper part of the sample, the upper shear box, and the rigid plate (N); $I_\sigma$ is the output data of digitally hydraulic pressure gauge of No. 1 hydraulic pump (MPa); $I_\tau$ is the output data of digitally hydraulic pressure gauge of No. 2 hydraulic pump (MPa); $A_j$ is measured area of the shear area (mm$^2$); $A_j$ is the piston area of the horizontal jack (mm$^2$); and $A_v$ is the area of the flat jack (mm$^2$).

(XI) Calculating normal stiffness $K_n$ and shear stiffness $K_s$ of the structural plane, according to the formula II:

$$\left. \begin{array}{l} K_n = \dfrac{\partial \sigma}{\partial \Delta v} \\ K_s = \dfrac{\partial \tau}{\partial \Delta u} \end{array} \right\} \quad \text{Formula II}$$

Where, $K_n$ is normal stiffness of structural plane (GPa·m$^{-1}$); $K_s$ is shear stiffness of structural plane (GPa·m$^{-1}$); $\Delta v$ is normal displacement (mm); $\Delta u$ is shear displacement (mm).

The beneficial effect of the invention is:

I. The present invention applied a method that shear box is a mold for sample preparation, a mold that is free from water curing, which is effectively reduced the disturbances of the sample of structural plane. Sample preparation is conducted after sample fastening bolt and fastening rubber gasket fixed structural plane, which can avoid sample preparation error caused by the excessive settlement and uneven settlement.

II. The present invention connected together the vertical loading system, the horizontal loading system and the shearing system through the frame system. The present invention do not need to repeatedly load and unload the jack during the process of experiment, the output and direction of jack are stable and accurate. Therefore, the operability of the experiment and the accuracy of the experiment's results are both improved.

III. The invention applied flat jack and rigid plate to exert normal load, which ensured that the center line of normal load is perpendicular to the sheared plane and passed through the center of it, avoiding eccentric moment and conquering the flaws of the traditional method.

IV. The invention applied rolling ball and guide rail to ensure the shear box pedestal can only freely slip along the shearing direction, so as to avoid lateral displacement that appeared during the shearing process, which is further increased the accuracy and reliability of the result.

VI. The invention applied digitally hydraulic gauge to record vertical pressure and horizontal pressure and also applied displacement transducer to measure vertical displacement and horizontal displacement, so as to achieve the digitally synchronous acquisition of the experimental data.

Mark number: 1: frame column bolts; 2: fixed bolt of flat jack; 3: nozzle of flat jack; 4: apparatus top panel; 5: flat jack; 6: rigid plate; 7: limited plate; 8: upper shear box; 9: fastening bolt holes; 10: lower shear box; 11: apparatus frame columns; 12: horizontal jack pedestal; 13: fixed bolt of horizontal jack; 14: horizontal jack; 15: nozzle of horizontal jack; 16: slot for horizontal displacement transducer; 17: shear box pedestal; 18: guide rail; 19: rolling steel ball; 20: apparatus pedestal; 21: sample of structural plane; 22: shear box grouting hole; 23: sample fastening bolt; 24: fastening rubber gasket.

DETAILED DESCRIPTION OF THE EMBODIMENTS

Figure 1:
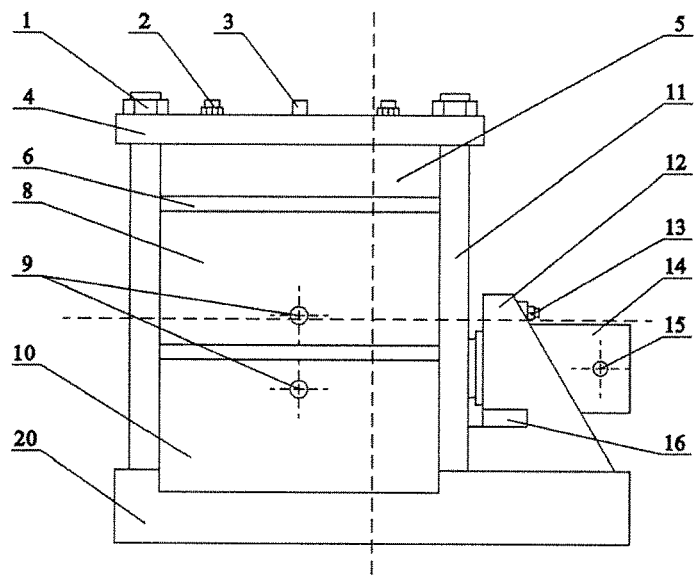
FIG. 1 is a front view of the present invention.
Figure 2:
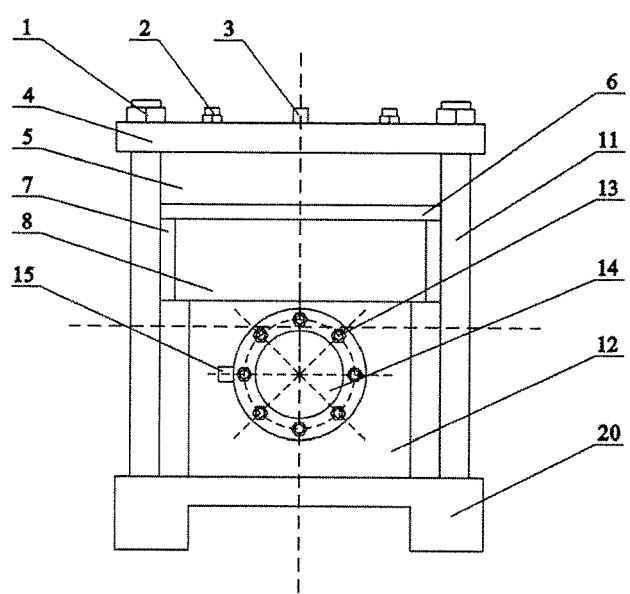
FIG. 2 is a right view of the present invention.
Figure 3:
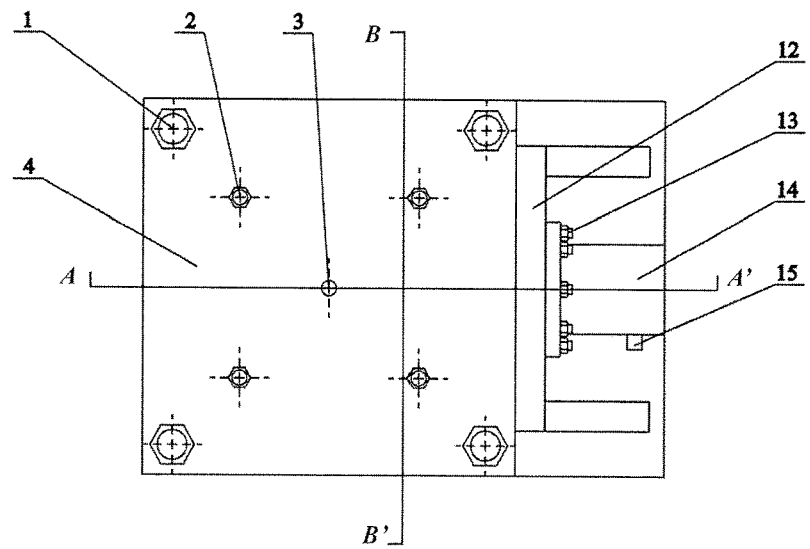
FIG. 3 is a top view of the present invention.
Figure 4:
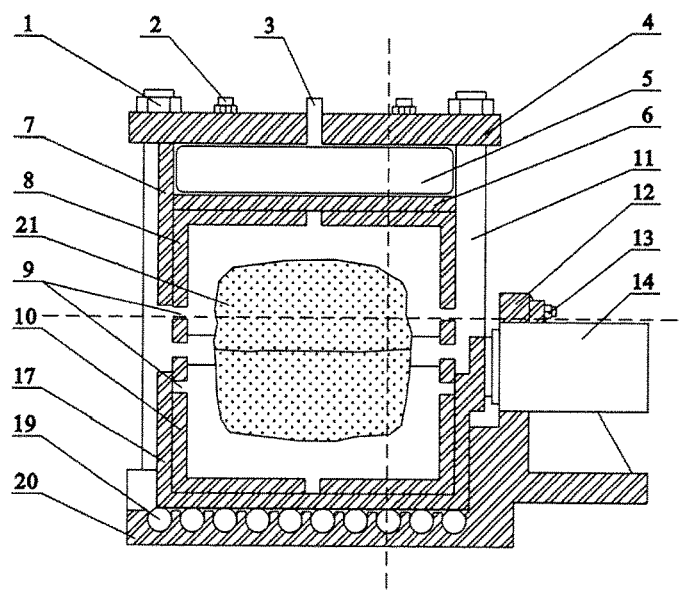
FIG. 4 is a sectional view of FIG. 3 taken along line A-A
Figure 5:
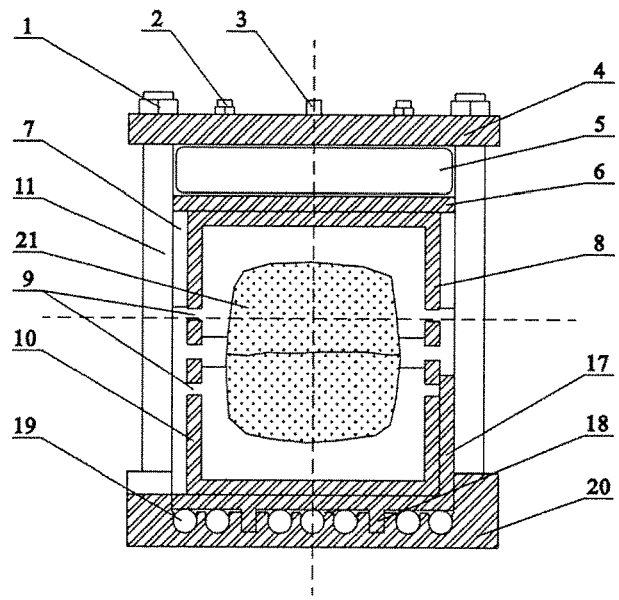
'
FIG. 5 is a sectional view of FIG. 3 taken along line B-B'.
Figure 6:
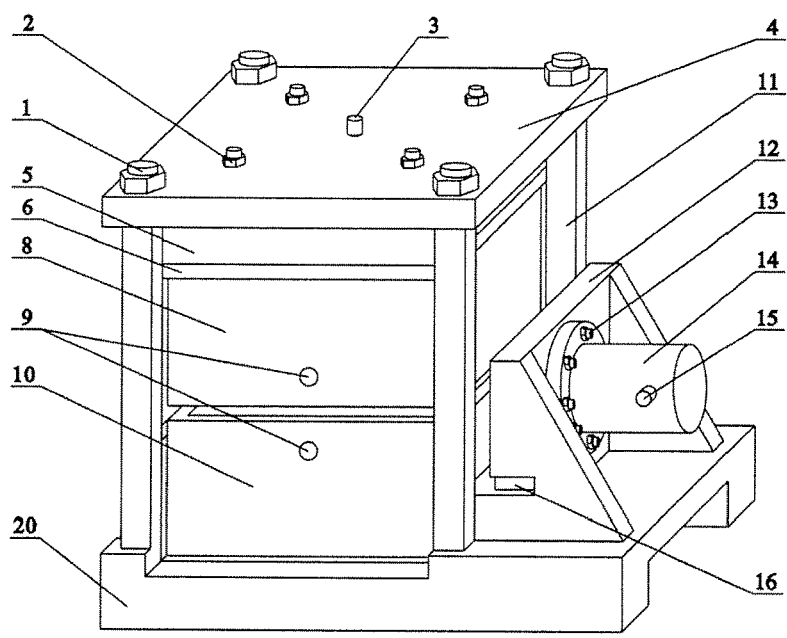
FIG. 6 is a stereogram of the present invention.
Figure 7:
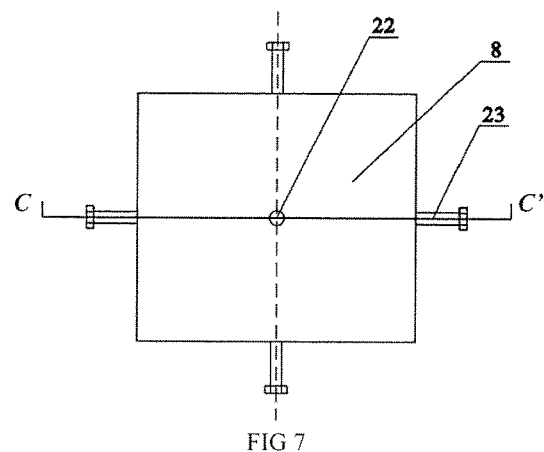
FIG. 7 is a top view of the shear box.
Figure 8:
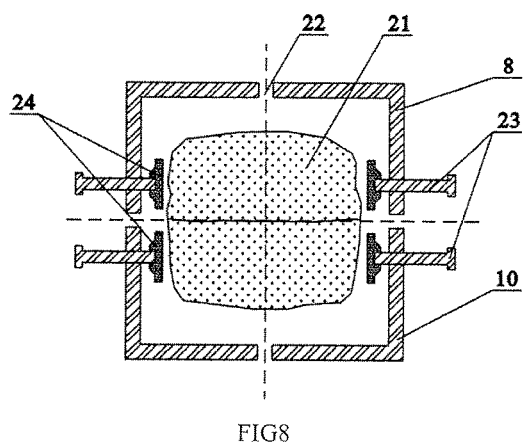
FIG. 8 is a sectional view of FIG. 7 taken along line C-C'.
Figure 9:
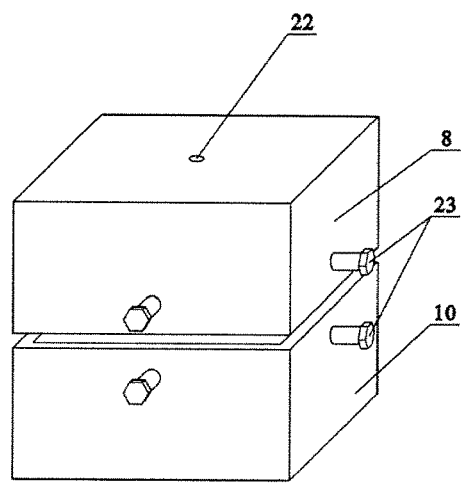
FIG. 9 is a stereogram of the shear box.

Example 1 is described in further detail of the present invention with referring to the FIGS. 1 to 9.

An integrated style shear apparatus for rock structural plane comprises frame system, vertical loading system, horizontal loading system and shearing system; Both of vertical loading system and horizontal loading system are fixed on, shearing system is installed inside the frame system. The shearing system is used to prepare the sample of structural plane and actualize the shear test, the vertical loading system and the horizontal loading system are used to provide normal stress and shear stress for the shearing system respectively.

The frame system comprises apparatus pedestal 20, apparatus frame columns 11, apparatus top panel 4 and limited plate 7. The bottom of the apparatus frame columns 11 are fixed on the apparatus pedestal 20 and the top of the apparatus frame columns 11 are detachably connected the apparatus top panel 4 through frame column bolts 1; the apparatus pedestal 20, the apparatus frame columns 11 and the apparatus top panel 4 formed the frame construction of the entire apparatus, providing operating space for vertical loading system, horizontal loading system and shearing system; limit plate 7 is fixed on the apparatus frame columns 11; the apparatus pedestal 20 is equipped with the guide rail groove along with the sheared direction.

The apparatus pedestal 20 is also equipped with sliding assisted device. And the sliding assisted device is combined with rolling steel ball 19 and supported rolling ball hole that located both in a row and uniformly in the surface of the apparatus pedestal 20; in the example, rolling steel balls 19 and its supported rolling ball hole are arranged as 7 columns*10 rows; the bottom of the shear box pedestals 17 are connected with rolling steel balls 19, so as to enable shear box pedestals 17 to conduct shear displacement with the promotion of horizontal loading system.

The vertical loading system comprises flat jack 5 and rigid plate 6; and the flat jack is fixed on the apparatus top panel 4 through fixed bolt of flat jack 2; the nozzle of flat jack 3 penetrated through the apparatus top panel 2 of the frame system and reached out its surface to connect oil pump; the rigid plate 6 is actively located at the underneath of the flat jack 5, so as to uniform and stable normal load that provided by the flat jack. The flat jacks 5 can conduct anti force support with the help of apparatus top panel 4 and exert normal stress on sample of structural plane 21.

The horizontal loading system comprises horizontal jack 14 and slot for horizontal displacement transducer 16; and the horizontal jack 14 is fixed on the horizontal jack pedestal 12 through fixed bolt of horizontal jack 13; the horizontal jack pedestal 12 loaded on the one side of the apparatus pedestal 20 and integrated with it; the horizontal jack 14 is capable of pushing the shear box pedestal 17 in the shear system, so as to conduct shear displacement; the slot for horizontal displacement transducer 16 is set in the horizontal jack pedestal 12; horizontal displacement transducer that is used to measure the horizontal displacement of shear system is fixed on the inside of the slot for horizontal displacement transducer 16; the nozzle of horizontal jack 15 is located at the outside of horizontal jack 14 to connect oil pump.

The shearing system comprises upper shear box 8, lower shear box 10 and shear box pedestal 17; the upper shear box 8 is horizontal limited by limit plates 7; the lower shear box 10 can be placed into the shear box pedestal 17 and upper shear box 8 is opened down while lower shear box 10 is opened up and both of them can integrate with shear box of the apparatus and form the effective space for sample of structural plane in shear box. The upper shear box 8 is passive shear box while the lower shear box 10 is the active shear box. And the shear box pedestal 17 is equipped with guide rail 18 which enable the shear box pedestal 17 to displace along with the apparatus pedestal 20.

The shear boxes are sample preparation mold which is free from stripping. Experiment can be conducted by pushing sample of structural plane 21 and shear boxes into shear box pedestal 17, which effectively reduced disturbance. The shear box pedestal 17 is equipped with guide rail 18 ensured that shear box pedestal 17 can only displace along with shear direction, which prevent shear direction change as the structural plane is not smooth.

Fastening bolt hole 9 are loaded all around the upper shear box 8 and lower shear box 10; fastening bolt hole 9 are equipped with sample fastening bolts 23; the inside end of the sample fastening bolt 23 is detachably loaded fastening rubber gasket 24, which can be used to fix sample of structural plane 21, avoiding sample preparation error caused by the excessive settlement and uneven settlement. When finishing the sample adjustment, backout all sample fastening bolts 23 and leave fastening rubber gaskets 24 with sample of structural plane in shear box.

The bottom of the upper shear box 8 and the lower shear box 10 are equipped with shear box grouting hole 22, which are used to inject high strength gypsum paste for preparing sample of structural plane, avoiding flaws that may be appeared in normal method, including destabilization and filling material that cannot be filed to the full. And the sample of structural plane 21 can be fast unloaded through the shear box grouting hole 22 when the experiment is over.

During the experiment, the fastening bolt hole 9 of the upper shear box 8 can be used to fix vertical displacement transducer, measuring and recording the vertical displacement of the upper shear box 8.

Example 2 is described in further detail of the experimental method of the present invention with referring to the FIGS. 1 to 9.

The present invention provide an experimental method by using the shear apparatus of implementation example 1, and includes the following steps:

(I). Sample placement: select appropriate sample of structural plane according to the effective space formed by the upper shear box and the lower shear box; brush a layer of mold oil equably inside the shear boxes; place the sample of structural plane into shear box and ensure that the shear direction is consistent with the long edge of the shear box.

(II). Sample adjustment: adjust the position of sample of structural plane and make the shear plane of it higher 5 mm than the frame of shear box and maintain horizontal; and then, apply the sample fastening bolt and fastening rubber gasket inside the shear box to fix the sample of structural plane.

(III). Sample preparation: inject high strength gypsum paste through the grouting hole located at the bottom of shear box; then, tamp and smooth the gypsum paste. Turn over the sample along with the shear box after gypsum paste's final setting, repeat the above steps to finish the remaining half of the sample's preparation; after finishing the sample preparation, backout all the sample fastening bolts.

(IV). Sample loading: pushing prepared sample along with shear boxes into the shear box pedestal of the apparatus and ensure that active shear box is in the lower position while the passive one in the upper position.

(V). Instrument hookup: Horizontal displacement transducer is installed on slot for horizontal displacement transducer of the apparatus; Vertical displacement transducer is installed on the fastening bolt hole of the upper shear box; the No. 1 manually hydraulic pump is connected with nozzle of flat jack and installed digitally hydraulic pressure gauge; the No. 2 manually hydraulic pump is connected with nozzle of horizontal jack and also installed digitally hydraulic pressure gauge. Finally, connected the above transducers and hydraulic gauge with computer and reset all monitoring data.

(VI). Exerting normal stress: using the No. 1 manually hydraulic pump to exert normal stress through vertical loading system and maintain a constant pressure after acquiring specified value.

(VII). Exerting Shearing stress: maintain a constant normal stress and using the No. 2 manually hydraulic pump to exert, step by step, shearing stress and increasing one level in every 30 s, until the sample is cut down. Criterion of cut down is that the output data of digitally hydraulic pressure gauge of No. 2 hydraulic pump is no longer rising or even falling; or the shear displacement increases continuously.

(VII). Measurement and description of shearing area: after the experiment, measuring the weight of upper part of the sample along with the upper shear box; using cellophane to cover the shearing plane, so as to outline the contour lines around the shearing areas and calculate the shearing area by using the coordinate paper.

(IX). Repeating the experiment: adjusting normal stress of different levels and repeat steps (II) to (V); then, test the rest of samples. It is suggested that the number of samples in each group is around 4 to 5.

(X). Calculating normal stress σ and shear stress τ according to the formula I:

$$\sigma = \frac{I_\sigma A_v + G}{A_j}$$
$$\tau = \frac{I_\tau A_h}{A_j}$$ 
Formula I where, σ is normal stress (MPa); τ is shear stress (MPa); G is total weight of upper part of the sample, the upper shear box, and the rigid plate (N); $I_\sigma$ is the output data of digitally hydraulic pressure gauge of No. 1 hydraulic pump (MPa); $I_\tau$ is the output data of digitally hydraulic pressure gauge of No. 2 hydraulic pump (MPa); $A_j$ is measured area of the shear area (mm²); $A_j$ is the piston area of the horizontal jack (mm²); and $A_v$ is the area of the flat jack (mm²).

Each sample's relation curve between shear displacement and shear stress can be obtained according to the experimental data, and then the curve's peak or stable value can be determined as the shear strength $\tau_{max}$ of the sample. According to each sample's shear strength $\tau_{max}$ and its corresponding normal stress σ, using optimal linear graphic method and coulomb's law τ=σtgφ+c to obtain shear strength parameters of rock structural plane: angle of internal friction φ and cohesion c.

(XI) Normal stiffness $K_n$ is defined as the normal stress which is need to generate unit normal deformation of structural plane, and its value is equal to the slope of any point's tangent line of relation curve between normal stress σ and the normal displacement Δv; shear stiffness $K_s$ is defined as the shear stress which is need to generate unit shear deformation of structural plane, and its value is equal to the slope of tangent line (before the peak) of relation curve between shear stress τ and the shear displacement Δu. The sample of structural plane's vertical pressure, horizontal pressure, vertical displacement and horizontal displacement can be synchronously collected by the digitally hydraulic pressure gauges and the displacement transducer; and then, normal stiffness $K_n$ and shear stiffness $K_s$ of the structural plane can be obtained according to the formula II:

$$K_n = \frac{\partial \sigma}{\partial \Delta v}$$
$$K_s = \frac{\partial \tau}{\partial \Delta u}$$ 
Formula II Where, $K_n$ is normal stiffness of structural plane (GPa·m⁻¹); $K_s$ is shear stiffness of structural plane (GPa·m⁻¹); Δv is normal displacement (mm); Δu is shear displacement (mm).

The invention claimed is:

1. An integrated style shear apparatus for a rock structural plane, comprises: a frame system, a vertical loading system, a horizontal loading system, and a shearing system, the vertical loading system and the horizontal loading system being fixed on the frame system, the shearing system being installed inside the frame system, the shearing system holding a sample of the rock structural plane, the vertical loading system and the horizontal loading system providing normal stress and shear stress for the shearing system, respectively;

wherein the frame system comprises: an apparatus pedestal, apparatus frame columns, an apparatus top panel, and a limiting plate, a bottom of each of the apparatus frame columns being fixed on the apparatus pedestal, a top of each of the apparatus frame columns are detachably connected to the apparatus top panel through frame column bolts;

wherein the shearing system comprises: an upper shear box, a lower shear box, and a shear box pedestal;

wherein placement of the upper shear box is horizontally limited by the limiting plate;

wherein the lower shear box can be placed into the shear box pedestal;

wherein the shear box pedestal is equipped with a guide rail enabling the shear box pedestal to move along with the apparatus pedestal; and wherein a top of the upper shear box and a bottom of the lower shear box have a grouting hole;

wherein the apparatus pedestal, the apparatus frame columns, and the apparatus top panel form the frame system of the integrated style shear apparatus, providing operating space for the vertical loading system, the horizontal loading system, and the shearing system; and wherein the limiting plate is fixed on the apparatus frame columns and the apparatus pedestal is equipped with a guide rail groove for accommodating the guide rail along a shearing direction perpendicular to the limiting plate.

2. The integrated style shear apparatus for the rock structural plane according to claim 1, wherein the apparatus pedestal is also equipped with a sliding assisting device, the sliding assisting device being an array of rolling ball holes supporting and supported rolling steel balls located both in the array and uniformly in contact with a bottom surface of the apparatus pedestal; and wherein the bottom surface of the apparatus pedestal connects with the rolling steel balls, so that the apparatus pedestal can conduct shear displacement with aid of the horizontal loading system.

3. The integrated style shear apparatus for the rock structural plane according to claim 1, wherein the vertical loading system comprises: a flat jack and a rigid plate;

wherein the flat jack is fixed on the apparatus top panel through a fixed bolt of the flat jack;

wherein a nozzle of the flat jack penetrates through the apparatus top panel of the frame system;

wherein the rigid plate is located underneath the flat jack, so that a uniform and stable normal load is provided by the flat jack.

4. The integrated style shear apparatus for the rock structural plane according to claim 1, wherein the horizontal loading system comprises: a horizontal jack and a slot for a horizontal displacement transducer;
wherein the horizontal jack is fixed on a horizontal jack pedestal through a fixing bolt of the horizontal jack;
wherein the horizontal jack pedestal being loaded on one side of the apparatus pedestal and being connected with the frame system;
wherein the horizontal jack is capable of pushing the apparatus pedestal in the shear system to conduct shear displacement;
wherein the slot for the horizontal displacement transducer is set in the horizontal jack pedestal, the horizontal displacement transducer measuring the horizontal displacement of the shear system and being fixed inside of the slot for the horizontal displacement transducer; and
wherein a nozzle of the horizontal jack is located on an outside of the horizontal jack.

5. The integrated style shear apparatus for the rock structural plane according to claim 1, wherein the upper shear box and the lower shear box are equipped with fastening bolt holes; each fastening bolt hole is equipped with one sample fastening bolt; and an inside end of each sample fastening bolt is detachably provided with a fastening rubber gasket.

6. The integrated style shear apparatus for rock structural plane according to claim 1, wherein the upper shear box is equipped with a vertical displacement transducer to record vertical displacement of the upper shear box.

7. A shear experimental method for a rock structural plane, wherein the experimental method utilized an integrated style shear apparatus for the rock structural plane, comprising: a frame system, a vertical loading system, a horizontal loading system, and a shearing system, the vertical loading system and the horizontal loading system being fixed on the frame system, the shearing system being installed inside the frame system, the shearing system holding a rock sample of the rock structural plane, the vertical loading system and the horizontal loading system providing normal stress and shear stress for the shearing system, respectively, including the following steps:
(I). place the sample of the rock structural plane into a shear box and ensure that a shear direction is consistent with a long edge of the shear box;
(II). adjust a position of the rock sample such that a shear plane of the rock sample is higher than a frame of the shear box and leveling the shear plane; then, apply sample fastening bolts and fastening rubber gaskets inside the shear box to fix the rock sample;
(III). inject high strength gypsum paste through a grouting hole located at a bottom of the shear box; then, tamp and smooth the gypsum paste; turn over the rock sample along with the shear box after a final setting of the gypsum paste, repeat steps (I)-(III) to a remaining half of the rock sample; after finishing-sample preparation, back out all the sample fastening bolts;
(IV). pushing the prepared rock sample along with the shear box into a shear box pedestal of the shear apparatus and ensure that the shear box under pressure is in a lower position while a passive shear box is in an upper position;
(V). install a horizontal displacement transducer on a slot for the horizontal displacement transducer of the shear apparatus; install a vertical displacement transducer on a fastening bolt hole of the shear box; a first manual hydraulic pump is connected with a nozzle of a flat jack and provided with a first digital hydraulic pressure gauge; a second manual hydraulic pump is connected with a nozzle of a horizontal jack and provided with a second digital hydraulic pressure gauge; connecting the horizontal displacement transducer, the vertical displacement transducer, and first and second digital hydraulic pressure gauges to a computer, and reset all monitoring data;
(VI). using the first manual hydraulic pump to exert normal stress through a vertical loading system and maintain a constant pressure after acquiring a specified pressure value;
(VII). using the second manual hydraulic pump to exert, step by step, shearing stress and increasing one level at a certain time, until the rock sample is cut down;
(VII). after the experiment, measuring a weight of an upper part of the rock sample along with the shear box; using cellophane to cover the shearing plane, so as to outline contour lines around shearing areas and calculate a shearing area by using coordinate paper;
(IX). adjusting normal stress of different levels and repeat steps (II) to (V); then, test more samples, a number of samples in each group is around 4 to 5;
(X). calculating normal stress σ and shear stress τ according to a first formula:

$$\sigma = \frac{I_\sigma A_v + G}{A_j}$$

$$\tau = \frac{I_\tau A_h}{A_j}$$

where, σ is normal stress (MPa); τ is shear stress (MPa); G is the weight of the upper part of the rock sample, the shear box, and the rigid plate (N); $I_\sigma$ output data of the first digital hydraulic pressure gauge of the first hydraulic pump (MPa); $I_\tau$ is output data of the second digital hydraulic pressure gauge of the second hydraulic pump (MPa); $A_h$ is a measured area of the shear area (mm$^2$); $A_j$ is a piston area of the horizontal jack (mm$^2$); and $A_v$ is an area of the flat jack (mm$^2$);
(XI) calculating normal stiffness $K_n$ and shear stiffness $K_s$ of the rock structural plane, according to a second formula:

$$K_n = \frac{\partial \sigma}{\partial \Delta v}$$

$$K_s = \frac{\partial \tau}{\partial \Delta u}$$

where, $K_n$ is a normal stiffness of the rock structural plane (GPa·m$^{-1}$); $K_s$ is a shear stiffness of the rock structural plane (GPa·m$^{-1}$); Δv is normal displacement (mm); and Δu is shear displacement (mm).

* * * * *